US008634629B2

(12) United States Patent
Wilson (10) Patent No.: US 8,634,629 B2
(45) Date of Patent: Jan. 21, 2014

(54) ESTIMATING RISK OF FUTURE BONE FRACTURE UTILIZING THREE-DIMENSIONAL BONE DENSITY MODEL

(75) Inventor: Kevin E. Wilson, Acton, MA (US)

(73) Assignee: Hologic, Inc., Bedford, MA (US)

( * ) Notice: Subject to any disclaimer, the term of this patent is extended or adjusted under 35 U.S.C. 154(b) by 942 days.

(21) Appl. No.: 12/452,310

(22) PCT Filed: Nov. 10, 2006

(86) PCT No.: PCT/US2006/043730
§ 371 (c)(1),
(2), (4) Date: Aug. 25, 2010

(87) PCT Pub. No.: WO2007/058918
PCT Pub. Date: May 24, 2007

(65) Prior Publication Data
US 2010/0310141 A1    Dec. 9, 2010

Related U.S. Application Data

(60) Provisional application No. 60/735,741, filed on Nov. 11, 2005.

(51) Int. Cl.
*G06K 9/00*    (2006.01)

(52) U.S. Cl.
USPC ........................................................ 382/132

(58) Field of Classification Search
USPC ......... 382/132; 378/21, 54–56, 196; 600/300, 600/407, 587
See application file for complete search history.

(56) References Cited

U.S. PATENT DOCUMENTS

| | | | |
|---|---|---|---|
| 4,947,414 | A | 8/1990 | Stein |
| 5,006,984 | A | 4/1991 | Steele |
| 5,040,199 | A | 8/1991 | Stein |
| 5,172,695 | A | 12/1992 | Cann et al. |
| 5,442,287 | A | 8/1995 | Kammann et al. |
| 5,772,592 | A | 6/1998 | Cheng et al. |
| 5,778,045 | A | 7/1998 | von Stetten et al. |
| 5,838,765 | A | 11/1998 | Gershman et al. |
| 5,850,836 | A | 12/1998 | Steiger et al. |
| 6,059,455 | A | 5/2000 | Cabral |
| 6,217,214 | B1 | 4/2001 | Cabral et al. |
| 6,282,258 | B1 | 8/2001 | Stein et al. |

(Continued)

FOREIGN PATENT DOCUMENTS

WO    WO2004/056270 A    7/2004

OTHER PUBLICATIONS

Dumas, R et. al., "Personalized Body Segment Parameters From Biplanar Low-Dose Radiography," pp. 1756-1763, Oct. 2005.*

(Continued)

*Primary Examiner* — Michelle L Le (57) ABSTRACT

A novel approach for analyzing a patient's body part of interest to assess bone strength and/or risk of future fracture includes obtaining a priori information regarding the body part of interest, performing X-ray absorptiometric scans of the patient's body part of interest and collecting X-ray absorptiometry data from the scans, constructing a three-dimensional model of the patient's body part of interest, by utilizing the a priori information along with the X-ray absorptiometric data, and performing measurements of various geometric parameters on the three-dimensional model for determining geometric and structural properties.

13 Claims, 3 Drawing Sheets

(56) References Cited

U.S. PATENT DOCUMENTS

| | | | |
|---|---|---|---|
| 6,385,283 | B1 | 5/2002 | Stein et al. |
| 6,496,557 | B2 | 12/2002 | Wilson et al. |
| 6,640,123 | B2 | 10/2003 | Warne et al. |
| 2005/0010106 | A1 | 1/2005 | Lang et al. |
| 2006/0204069 | A1 | 9/2006 | Le Bras et al. |
| 2007/0274442 | A1 | 11/2007 | Gregory et al. |

OTHER PUBLICATIONS

Bresson, X. et. al., "A Priori Information in Image Segmentation: Energy Functional Based on Shape Statistical Model and Image Information," pp. 425-428, 2003.*

Nov. 6, 2009 European search report in connection with counterpart European patent application No. 06837290.

Benameur, S., et al (2003), "3D/2D registration and segmentation of scoliotic vertebrae using statistical models", Computerized Medical Imagin and Graphics, vol. 27, No. 5, pp. 321-337.

Pardo X.M., et al (2004), "Integrating prior shape models into level-set approaches", Pattern Recognition Letters, vol. 25, No. 6, pp. 631-639.

Tang, T.S.Y., et al. (2005), "2D/3D Deformable Registration Using a Hybrid Atlas", Medical Image Computing and Computer-Assisted Intervention—MIC CAI 2005 Lecture Notes in Computer Science, vol. 3750, pp. 223-230.

Benameur, S., et at (2005), "Three-Dimensional Biplanar Reconstruction of Scoliatic Rib Cage Using the Estimation of a Mixture of Probabilistic Prior Models", IEEE Transactions on Biomedical Engineering, vol. 52, No. 10, pp. 1713-1728.

Dumas, R., et at (2005), "Personalized Body Segment Parameters From Biplaner Low-Dose Radiography", IEEE Transactions on Biomedical Engineering, vol. 52, No. 10, pp. 1756-1763.

Bresson, X. et al, A Priori Information in Image Segmentation: Energy Functional Based on Shape Statistical Mode and Information, ICIP 2003, Proceedings, 2003 International Conference on Image Processing, vol. 3, pp. 425-428, Sep. 2003.

Dumas, R. et al., "Personalized Body Segment Parameters From Biplanar Low-Dose Radiography", Biomedical Engineering, IEEE Transaction, vol. 52, Issue 10, pp. 1756-1763, Oct. 2005.

\* cited by examiner

ESTIMATING RISK OF FUTURE BONE FRACTURE UTILIZING THREE-DIMENSIONAL BONE DENSITY MODEL

CROSS-REFERENCE TO RELATED APPLICATION

This application claims the benefit of U.S. provisional application Ser. No. 60/735,741, filed Nov. 11, 2005, the entire contents of which are hereby incorporated by reference herein.

TECHNICAL FIELD

This disclosure relates to X-ray absorptiometry. In particular, the disclosure relates to use of information obtained through X-ray absorptiometry techniques along with other information to assess the condition of, and risk of injury to, a bone (for example, a femur, spine, forearm, etc.).

DESCRIPTION OF RELATED ART

Hip fracture is a serious osteoporotic injury and a significant public health concern, especially in industrialized countries which are currently in the midst of an aging trend of the population. Hip fracture is a debilitating injury for the patient, and the hundreds of thousands of hip fracture injuries each year constitute a significant cost to society.

A hip fracture is typically a break near the top of the thighbone (or femur) where it angles into the hip socket. In many instances, a patient who experiences a hip fracture from an accident such as, for example, a fall, was particularly susceptible to the injury because of weakened bone strength of the femur which depends on bone mineral density (BMD) and bone architecture. While age is a factor, a patient need not be a senior citizen to suffer a hip fracture injury. Other factors which contribute to the risk of hip fracture injury include gender, heredity, nutrition, personal habits, physical and/or mental impairment, medication, etc.

In many instances it is desirable to identify whether a patient is subject to a high risk of hip fracture injury. Preventive measures, such as in the form of supplemented diet, physical activity, adjusted lifestyle and living conditions, etc., may be taken to minimize the risk of hip fracture injury.

Bone densitometry (that is, study of BMD) is often used along with consideration of other risk factors (such as age, gender, heredity, nutrition, personal habits, physical and/or mental impairment, medication, etc.) to assess the future risk to a patient of hip fracture. However, techniques which are based only on BMD data of the bone without considering additional properties of the bone such as the bone's structure or architecture can result in an incomplete (and perhaps inaccurate) assessment of risk of fracture to a patient.

Multi-dimensional analysis of a patient's femur which includes three dimensional geometric and structural properties can be obtained using CT (computed tomography) or MR (magnetic resonance) systems. For example, techniques for analyzing a bone for fracture risk utilizing structural and BMD data obtained from CT are discussed in U.S. Pat. No. 5,172,695 to Cann et al. and Lang T F, Keyak J H, Heitz M W, Augat P, Lu Y, Mathur A, Genant H K. "Volumetric quantitative computed tomography of the proximal femur: precision and relation to bone strength." Bone. 1997 July; 21(1):101-08, the entire contents of each of which are incorporated herein by reference. However, techniques centering on CT or MR systems have relatively high cost and limited accessibility.

Dual X-ray absorptiometry (DXA) can also be used in bone densitometry. Techniques for determining bone fracture risk utilizing X-ray absorptiometry data are discussed in U.S. Pat. No. 6,385,283 to Stein et al. (the entire contents of which are incorporated by reference herein). DXA systems have relatively lower cost and higher accessibility as compared to CT or MR systems. DXA bone densitometers manufactured by Hologic, Inc. (Bedford, Mass.) and similar machines available from others (such as LUNAR Corporation and Norland Corporation) are commercially available for scanning a patient's hip, spine or another body part and perhaps classifying the risk to the patient of a future fracture.

The following references (the entire contents of which are incorporated by reference herein) discuss some exemplary studies by Beck et al. of femurs using DXA techniques.

Beck T J, Ruff C B, Warden K E, Scott W W Jr., Rao G U, "Predicting femoral neck strength from bone mineral data. A structural approach," Invest Radiol. (1990 January) 25(1):6-18.

Beck T J, Mourtada F A, Ruff C B, Scott W W Jr., Kao G., "Experimental testing of a DEXA-derived curved beam model of the proximal femur," J Orthop Res. (1998 May) 16(3):394-98.

Beck T J, Ruff C B, Mourtada F A, Shaffer R A, Maxwell-Williams K, Kao G L, Sartoris D J, Brodine S., "Dual-energy X-ray absorptiometry derived structural geometry for stress fracture prediction in male U.S. Marine Corps recruits," J Bone Miner Res. (1996 May) 11(5):645-53.

Beck T J, Looker A C, Ruff C B, Sievanen H, Wahner H W, "Structural trends in the aging femoral neck and proximal shaft: analysis of the Third National Health and Nutrition Examination Survey dual-energy X-ray absorptiometry data," Bone Miner Res. (2000 December) 15(12):2297-2304.

Beck et al. used two-dimensional (2-D) images of the femur, generated from areal BMD measurements obtained through conventional DXA scan, to measure geometric parameters thereon which supplement the areal BMD measurements and other information for estimating risk of fracture. Similarly, and in Faulkner K G, Cummings S R, Black D, Palermo L, Gluer C C, Genant H K, "Simple measurement of femoral geometry predicts hip fracture: the study of osteoporotic fractures," J Bone Miner. Res. (1993 October) 8(10):1211-17, (the entire contents of which are incorporated by reference herein) areal measurements of geometry from a DXA scan were used to predict future fracture risk. Such areal BMD measurements and 2-D images, however, can be affected by patient positioning and individual anatomic variations. Therefore, the geometric parameters measured using the 2-D images can be unacceptably inconsistent.

More recently, three-dimensional (3-D) reconstruction techniques using X-ray absorptiometry measurements have been developed for studying a femur. While the images reconstructed using such techniques are more consistently reliable, there is a need for improvements to, and refinements of, 3-D X-ray absorptiometry techniques for assessing bone strength and fracture risk, including techniques for measurement of various geometric parameters for structural analysis.

SUMMARY

The disadvantages of assessing risk to a specific patient of future bone fracture by referring to geometric parameters measured on one or more two-dimensional DXA images, such as performed by Beck, Faulkner, and others, can be avoided by developing a three-dimensional model of the patient's bone of interest, utilizing a priori information, such as a statistical atlas of the body part of interest, and in addition data from X-ray absorptiometric scans of the patient's body part of interest.

While such a three-dimensional model is an estimate of the patient's bone of interest, a three-dimensional bone density model developed in this manner presents true density information (in contrast to areal density information obtained through conventional 2-D X-ray absorptiometric images) and three dimensional geometric properties, and therefore is more consistently accurate and reliable information (than two-dimensional DXA images) for determining structural properties such as cross sectional moment of inertia, section modulus, buckling ratio, etc., as well as other properties related to bone strength.

Figure 1:
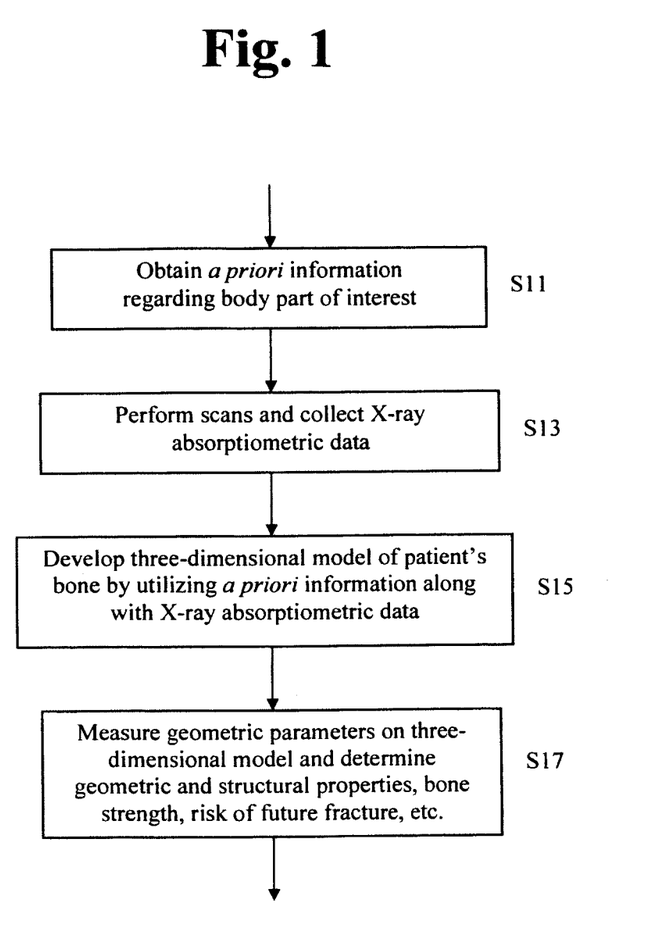
FIG. 1 shows a flow chart of a method for analyzing a patient's bone to assess risk of future fracture, according to one example.

According to one example (FIG. 1), a method for analyzing a patient's body part of interest to assess bone strength and/or risk of future fracture can include the following: obtain a priori information regarding the body part of interest (such as an anatomical or statistical atlas) (step S11); perform X-ray absorptiometric scans of the patient's body part of interest and collect X-ray absorptiometry data from the scans (step S13); construct a three-dimensional model of the patient's body part of interest, by utilizing the a priori information along with the X-ray absorptiometric data (step S15); and after the three-dimensional model is constructed, perform measurements of various geometric parameters on the three-dimensional model for determining geometric and structural properties (for example, cross sectional moment of inertia, section modulus, buckling ratio, etc.) (step S17).

The subject matter of this disclosure can be integrated in a system including a bone densitometer.

BRIEF DESCRIPTION OF THE DRAWINGS

The features of the present application can be more readily understood from the following detailed description with reference to the accompanying drawings wherein.

DETAILED DESCRIPTION

This disclosure provides improved tools for assessing risk of future fracture of a patient's hip, spine, etc. For example, a tool for analyzing a patient's femur may construct a three-dimensional (3-D) bone density model of the patient's femur by utilizing a priori information (such as an anatomical atlas of femurs) and measurements from X-ray absorptiometry (single or dual energy) scans of the patient's hip at several angles (for example, two to five), and then perform measurements on the 3-D bone density models of various geometric parameters for structural analysis.

Specific terminology is employed for the sake of clarity in the discussion of examples and embodiments herein. However, this patent disclosure is not intended to be limited to the specific terminology so selected and it is to be understood that each specific element includes all technical equivalents that operate in a similar manner.

As mentioned above, a priori information such as from an anatomical atlas is utilized to construct a 3-D model of a specific patient's hip (or spine, forearm, etc.). An anatomical atlas comprises shape data for an anatomical organ or part, and may represent data of a standard anatomical organ or part. Thus, an anatomical atlas can be used as a tool to model human anatomy and to represent normal anatomical variations. For example, an anatomical atlas can be registered to individual patient images to facilitate medical image interpretation and analysis. When an atlas has been registered to a particular image or set of images, structures of interest can be labeled and extracted for further analysis.

Many of such anatomical atlases are commercially available and/or accessible on-line. In addition, the atlas can be generated by using data obtained through a data acquisition system such as a CT scan system. The atlas may be formed from a statistical dataset for a number of samples of the anatomical organ or part of interest (that is, from a number of patients or subjects). Such an atlas is referred to herein as a "statistical atlas". The statistical atlas typically can be utilized to form a graphical model or other visual representation of an anatomical organ or part of interest.

A statistical atlas of, for example, a femur is preferably formed by utilizing the following method. A statistical dataset may be obtained from, for example, CT scans of a plurality of (preferably diverse) samples (that is, hips of plural patients or human subjects). The statistical dataset is processed by applying principal component analysis (PCA) shape modeling. The PCA shape modeling technique determines shape constraints represented by a number of eigenvectors which correspond to modes of variation of femurs (each mode corresponding to a hip type). Thereafter, each specific femur can be represented by a set of expansion coefficients of the eigenvector representation. See, for example, Kilian M. Pohl, Simon K. Warfield, Ron Kikinis, W. Eric L. Grimson, and William M. Wells, "Coupling Statistical Segmentation and PCA Shape Modeling," Medical Image Computing and Computer-Assisted Intervention—MICCAI, Sep. 26-29, 2004, Proceedings, Part I, Volume 3216, pp. 151-159, the entire contents of which are incorporated herein by reference.

As mentioned above, a statistical atlas can comprise data for one or more standard or typical femurs. However, it should be apparent that the femur of a specific patient may, in many instances, deviate from the standard or typical femur(s). Therefore, the statistical atlas model is used merely as a priori reference information which is utilized in combination with measurements, such as X-ray absorptiometry data, of the specific patient's femur. Any of the conventional X-ray densitometers can be used for obtaining the X-ray absorptiometry data, but the preferred embodiment uses an X-ray densitometer with a rotating C-arm (such as Hologic QDR4500A) so that the bone can be viewed from different angles without moving the patient.

Figure 2A:
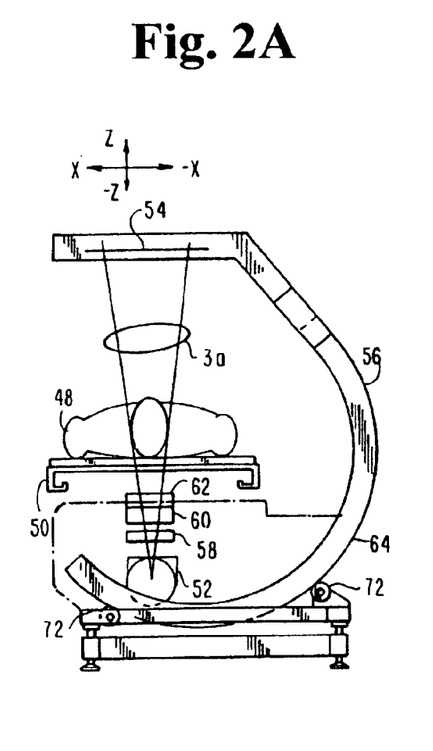
FIGS. 2A and 2B show schematic views of a C-arm scanner for a bone densitometer, according to one example of the present application, configured for a posterior-anterior spine scan and a hip scan, respectively.
Figure 2B:
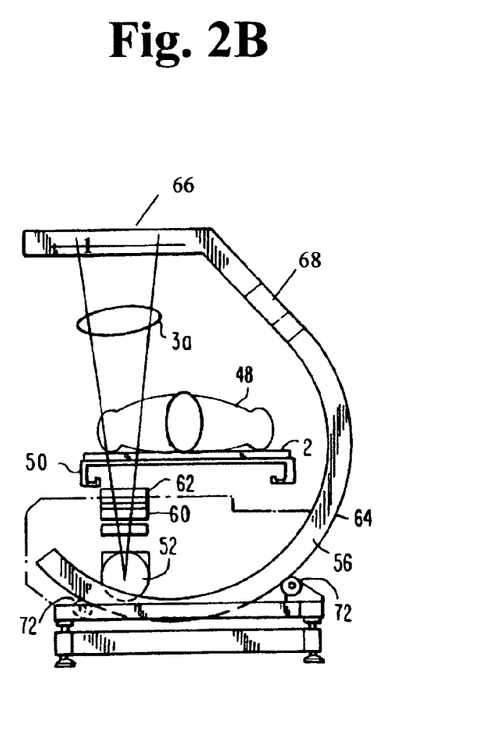
Figure 2C:
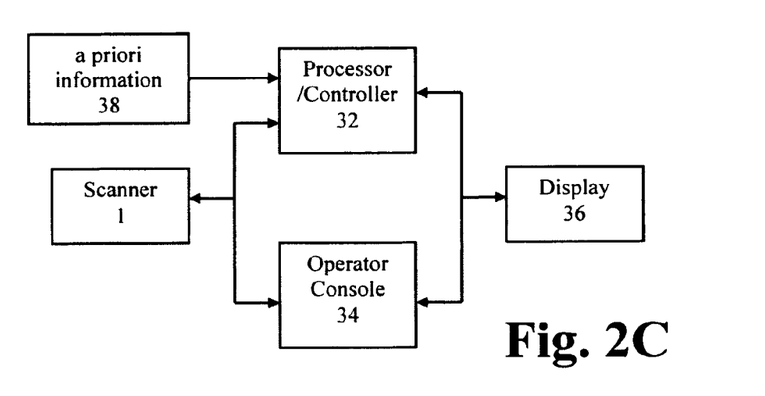
FIG. 2C shows a block diagram of additional components of the bone densitometer shown in FIGS. 2A and 2B.

FIGS. 2A-2C illustrate an example of an X-ray densitometer into which the subject matter of this disclosure can be integrated. The system of FIGS. 2A-2C is one example (QDR4500A) in the QDR series of bone densitometers commercially available in this country from Hologic, Inc. of Bedford, Mass. Additional bone densitometers are described in, for example, U.S. Pat. Nos. 5,838,765, 5,850,836, 6,059,455, 6,217,214, 6,282,258, 6,385,283, 6,496,557 and 6,640,123, the entire contents of each of which are hereby incorporated by reference.

In the scanner 1 of FIGS. 2A and 2B, a patient 48 can lie in the supine position during scanning on patient table 50. X-rays from an x-ray source 52 located beneath table 50 pass through patient 48 and are received by a detector 54 having an array of detector elements located above patient 48. Each detector element responds to x-rays at respective angular positions within a fan beam of x-rays. Both x-ray source 52 and detector 54 are supported on C-arm 56 which maintains a selected source-to-detector distance and alignment.

C-arm 56 includes a central portion 64 which can be combined with an integrating structure to support x-ray source 52, slit collimator 58, x-ray beam modulator 60 and x-ray beam attenuator 62. A removable upper arm portion 66 houses x-ray detector 54, using a bracket interface 68. C-arm 56 rotates about a rotational axis which extend along the Y-axis (normal to the sheet) and is at the geometric center of portion 64 of C-arm 56. C-arm 56 can rotate essentially within its own volume about the rotational axis. In addition, C-arm 56 rides on rollers 72, and moves along the Y-axis, along the length of a patient and thus along the patient's spine.

Patient support table 50 can be translatable along all three axes—the longitudinal (Y-axis), the transverse (X-axis), and the vertical (Z-axis). C-arm 56 can move in conjunction with patient table 50. The motions of table 50 in the transverse and vertical directions (along the X-axis and along the Z-axis) help C-arm 56 clear table 50 when rotating between the various positions of C-arm 56 used for different types of patient procedures.

As carried on C-arm 56, x-ray source 52 and detector 54 have a 2-axis motion with respect to patient 48 to carry out scans. Motion in the longitudinal Y direction moves them along the patient axis as defined by the spine. A second motion, about the rotational axis, rotates them around the patient, the center of rotation being determined by the C-arm 56 (more specifically, by the outer radius of C-arm 56) and the method of rotation employed. The center of rotation is not the focal spot in the X-ray tube, but rather is spaced from the focal spot by a significant distance.

Detector 54 in this example comprises a number of detector elements. The signals produced by the detector elements in response to x-rays impinging thereon are digitized by an analog to digital (A/D) converter and are stored on disk or another storage device (not shown). Processor 32 (FIG. 2C) which is coupled to the scanner 1 processes the signals from the A/D converter into density representations, and/or images, and/or reports of measured and/or calculated parameters, using principles disclosed in the material referenced in the background section of this disclosure, and then outputs the density representations, images, and/or reports to a display 36 or another output device (not shown). Processor 32 can perform assorted functions (including control various components of the bone densitometer) based on one or more programs of instructions and user input supplied through operator console 34.

The scanner 1 may take images of the patient's hip at a few different positions (for example, 2 to 5 scans). Additional scans can also be taken (that is, more than 5). However, the decision whether to include additional scans should consider the additional time of such additional scans (including setup time for each of the positions) as weighed against the additional information to be obtained from the additional scans. On the other hand, a single scan of the specific patient's femur may be used with a priori information from, for example, a statistical atlas to construct a 3-D bone density model of the patient's femur. It should be understood, however, that the 3-D model constructed utilizing data from a single scan is of course less accurate than a 3-D model constructed utilizing data from multiple scans.

In one example, scans of the patient's hip may be taken at three angles (such as 0°, +15° and −20°, measured with respect to a vertical axis normal to the plane of the table), using a complete, single or dual energy scan at each angle. The data collected by the imager 20 of the scanner 1 is supplied to the processor (or processing subsystem) 32 which processes the data in accordance with one or more programs of instructions. Techniques utilizing the X-ray absorptiometry data to construct density representations and/or images, and/or generate reports of measured and/or calculated parameters are well-understood and therefore not repeated herein in the interest of clarity. See, for example, U.S. Pat. Nos. 4,947,414, 5,040,199 and 5,778,045, each of which is incorporated herein by reference in its entirety.

The views may be taken with a dual or single energy densitometer. An advantage of dual energy is that soft-tissue can be removed. Single energy can be used for one or more views, because mutual information allows for the image to have "noise" (for example, from soft tissue). Typically, these images are fan-beam images (although cone beam images of mini-C-arms can also be used), very similar to CT scout scans.

The X-ray absorptiometry data and/or images are utilized by the processor 32 along with a priori information from source 38 to construct the 3-D model. Any of various methods for constructing the 3-D model from a priori information can be used.

In one approach, each 2-D X-ray absorptiometry image is projected at the corresponding angle (at which the corresponding scan was taken) onto the 3-D model. In the example wherein PCA shape modeling is utilized to generate a statistical atlas of femurs, 2-D X-ray absorptiometry data is processed to generate expansion coefficients for the eigenvector representation of the 3-D model (see discussion in Pohl et al.).

In a preferred embodiment (FIG. 3), a 3D volume model is generated based on the population average (a statistical atlas) of the bone tissue of the femur (step S31). In this embodiment, generally, no soft tissue is present in the model, and this is usually referred to as "segmented", meaning soft tissue and bone have been separated. There are differing possible representations that can be used for the model. One example is a tetrahedral mesh with Bernstein polynomial density functions. Another example is cubes of differing density. The model is chosen based on computational considerations and anatomical considerations, that is, not only whether the model is easy to calculate but also whether it sufficiently captures the important features of the anatomy.

Figure 3:
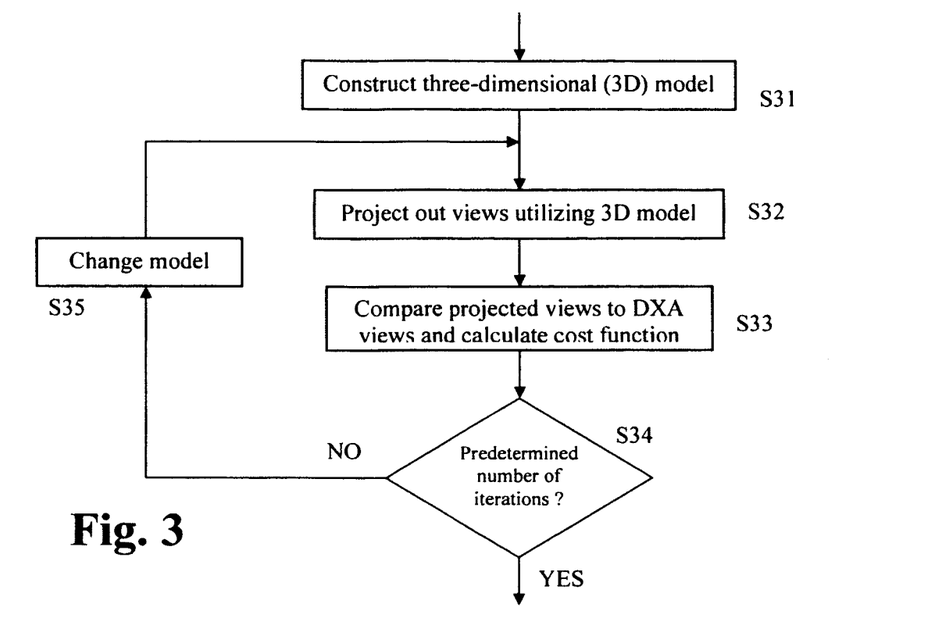
FIG. 3 shows a flow chart of a method for generating a 3-D bone density model.

Next, the same views as taken by DXA are projected out utilizing the 3D model (step S32). The projections are compared to the DXA views and a cost function (for example, a goodness of fit measure) is calculated (step S33), for example, using a method called "mutual information." If a predetermined number of iterations has not yet been performed (step S34, NO), the 3D volume model is changed (step S35) and steps S32 through S34 are repeated. Steps S32 through S35 are repeated a predetermined number of times (for example, thousands) to find the best "fit", or minimum "cost". Any of various well-known minimization techniques, such as "Ameoba" or "simulated annealing" [see, for example, "Numerical Recipes" in *C: The Art of Scientific Computing*, 2nd edition Chapter 10 by William H. Press, Brian P. Flannery, Saul A. Teukolsky, and William T. Vetterling (Cambridge University Press 1992)], can be utilized to minimize the cost function and find the best fit in n-dimensional space.

For example, a pose-and-scale approach minimizes over seven (7) dimensions. "Pose" corresponds to three translational dimensions and three rotations with respect to a position and orientation of a rigid body. "Scale" is simply the scale factor (size). In addition, there are the number of eigenvectors which describe the anatomical variation of the atlas. In one exemplary implementation, the first 7-20 eigenvectors capture most of the anatomical variations (that is, each additional eigenvector is less important). The cost function was minimized over the pose-and-scale (7 total) and 12 model eigenvectors were used, whereby the minimum was found in 19-dimensional space.

In another example, an anatomical atlas is utilized to generate a 3-D model, and conventional techniques are utilized with the X-ray absorptiometry data of the patient's hip to construct 2-D images. Reference markers are identified on each 2-D image and then the 2-D image is mapped to the 3-D model by registering the markers on the 2-D image with corresponding points of the 3-D model. Once the reference markers are registered to the 3-D model, the remaining points of the 2-D image of the patient's hip may be utilized to adjust the 3-D model in order to develop the 3-D model of the patient's femur.

In addition, the following references (the entire contents of each of which are incorporated by reference herein) discuss additional techniques for registering and mapping 2-D images onto a 3-D model, in order to adapt the model with information from the 2-D images.

S. Kolta, A. Le Bras, D. Mitton, V. Bousson, J. A. de Guise, J. Fechtenbaum, J. D. Laredo, C. Roux, W. Skalli, "Three-dimensional X-ray absorptiometry (3D-XA): a method for reconstruction of human bones using a dual X-ray absorptiometry device," Osteoporos Int (2005) 16: 969-976.

A. Le Bras, S. Laporte, V. Bousson, D. Mitton, J. A. De Guise, J. D. Laredo, W. Skalli, "3D reconstruction of the proximal femur with low-dose digital stereoradiography." Comput Aided Surg., 9(3):51-7 (2004).

International Publication No. WO2004056270 A1 (Le Bras et al.).

K. Ramamurthi, and J. Prince, "Tomographic Reconstruction for Truncated Cone Beam Data Using Prior CT Information," MICCAI (2) 2003: 134-141.

O. Sadowsky, K. Ramamurthi, J. Yao, J. Prince, and R. H. Taylor, "An Atlas-Assisted Method for Limited-Angle Cone-Beam Tomography." Symposium on Biomedical Information Science and Technology Initiative (BISTI), National Institutes of Health, Bethesda, Md. (November 2003).

O. Sadowsky, K. Ramamurthi, J. L. Prince, and R. H. Taylor, "Using anatomical models and fast rendering algorithms for C-arm pose recovery and cone-beam tomographic reconstruction of bone anatomy," presented at Computer Assisted Orthopaedic Surgery, Helsinki, June 2005.

O. Sadowsky, J. Cohen, and R. H. Taylor "Rendering Tetrahedral Meshes with Higher-Order Attenuation Functions for Digital Radiograph Reconstruction," presented at IEEE Visualization, Minneapolis, Minn., 2005.

O. Sadowsky, J. Cohen, and R. H. Taylor "Projected Tetrahedra Revisited: A Barycentric Formulation Applied to Digital Radiograph Reconstruction Using Higher-Order Attenuation Functions," *IEEE Trans. Visualization and Computer Graphics*, (2006).

O. Sadowsky, K. Ramamurthi, L. M. Ellingsen, G. Chintalapani, J. L. Prince, R. H. Taylor, "Atlas-Assisted Tomography: Registration of a Deformable Atlas to Compensate for Limited-Angle Cone-Beam Trajectory", *International Symposium on Biomedical Imaging (ISBI)*, 2006.

S. J. Timoner, "Compact Representations for Fast Nonrigid Registration of Medical Images," MIT Ph.D. Thesis, 2003.

S. J. Timoner, P. Golland, R. Kikinis, M. E. Shenton W. E. L. Grimson and W. M. Wells, "Performance Issues in Shape Classification," Medical Image Computing and Computer-Assisted Intervention, MICCAI'02, Accepted for Publication, 2002 (Springer-Verlag).

J. Yao, R. H. Taylor, R. P. Goldberg, R. Kumar, A. Bzostek, R. V. Vorhis, P. Kazanzides, A. Gueziec, and J. Funda, "A Progressive Cut Refinement Scheme for Revision Total Hip Replacement Surgery Using C-arm Fluoroscopy," presented at Medical Image Computing and Computer-Assisted Interventions (MICCAI-99), Cambridge, England, 1010-1019, Oct. 11-13, 1999.

J. Yao and R. Taylor, "Tetrahedral Mesh Modeling of Density Data for Anatomical Atlases and Intensity-Based Registration", presented at Medical Image Computing and Computer-Assisted Interventions (MICCAI 2000), Pittsburgh, Pa. (Oct. 11-14, 2000), pp. 531-540.

J. Yao, R. H. Taylor, R. P. Goldberg, R. Kumar, A. Bzostek, R. V. Vorhis, P. Kazanzides, and A. Gueziec, "A Progressive Cut Refinement Scheme for Revision Total Hip Replacement Surgery Using C-arm Fluoroscopy," *J. Computer Assisted Surgery*, vol. 5, 2000.

J. Yao, "Building Tetrahedral Mesh Model from Bone Contours," ERC, Johns Hopkins Univ. ERC-2000-01, 2000.

J. Yao and R. H. Taylor, "Reconstructing Hierarchical Tetrahedral Mesh Density Models of Bony Anatomy," presented at Medical Meets Virtual Reality 2001, Newport Beach, Calif., pp. 587-593, 2001.

J. Yao and R. Taylor, "Construction and Simplification of Bone Density Models," presented at SPIE Medical Imaging 2001, San Diego, Calif., 2001.

J. Yao and R. Taylor, "Reconstructing hierarchical tetrahedral mesh density models of bony anatomy," *Stud Health Technol Inform*, vol. 81, pp. 587-93, 2001.

J. Yao and R. H. Taylor, "Deformable registration between a statistical bone density atlas and X-ray images," presented at Second International Conference on Computer Assisted Orthopaedic Surgery (CAOS 2002), Santa Fe, Jun. 18-23, 2002.

J. Yao, "A statistical bone density atlas and deformable medical image registration", Ph.D. Thesis in Computer Science, The Johns Hopkins University, Baltimore: 2002.

J. Yao and R. H. Taylor, "A Multiple-Layer Flexible Mesh Template Matching Method for Non-rigid Registration between a Pelvis Model and CT Images," presented at SPIE Medical Imaging, San Diego, 1117-1124 (Feb. 15-20, 2003).

J. Yao, R. Taylor, "Assessing accuracy factors in deformable 2D/3D medical image registration using a statistical pelvis model", Proc. Ninth IEEE Int'l Conf. Computer Vision, vol. 2, pp. 1329-1334 (Oct. 13-16, 2003).

J. Yao and R. Taylor, "Deformable 2D-3D Medical Image Registration Using a Statistical Pelvis Model: Experiments and Accuracy Factors," *IEEE Transactions on Medical Imaging*, 2003.

J. Yao and R. H. Taylor, "Non-Rigid Registration and Correspondence in Medical Image Analysis Using Multiple-Layer Flexible Mesh Template Matching," *International Journal of Pattern Recognition and Artificial Intelligence (IJPRAI)*, vol. 17, 2003.

Accordingly, in the interest of clarity, this disclosure does not include a detailed discussion of all of the different approaches for registering and mapping 2-D images onto a 3-D model.

Various geometric parameters for structural analysis can be measured from the 3-D bone density model of the patient's femur. Use of such measurements to determine geometric properties for assessing the strength of the patient's femur is known in the art. For example, finite element analysis (such as discussed in U.S. Pat. No. 5,172,695 to Cann et al.) can be utilized to predict hip strength. Additionally, various geometric properties, such as cross sectional moment of inertia, section modulus, buckling ratio, etc., can be determined. Cross-sectional moment of inertia is an indicator of bone mass distribution. See, for example, U.S. Pat. No. 5,772,592 to Cheng et al., U.S. Pat. No. 5,006,984 to Steele, Martin R B et al., "Non-invasive measurement of long bone cross-sectional moment of inertia by photon absorptiometry," J Biomech. (1984) 17(3):195-201, Gilbert J A et al., "Cross-sectional moment of inertia of the distal radius from absorptiometric data," (1989) 22(6-7):751-54, and Corcoran T A et al., "Calculation of cross-sectional geometry of bone from CT images with application in postmenopausal women," J Comput Assist Tomogr. (1994 July-August) 18(4):626-33 (each of which is incorporated herein by reference). Section modulus is an indicator of maximum bending stress at a cross section. See, for example, U.S. Pat. No. 6,442,287 to Jiang et al., http://guide.stanford.edu/96reports/96clin3.html, "Femoral Geometry and Structure assessment using DXA," and http://guide.stanford.edu/96reports/96clin4.html, "Femoral properties—changes after spinal cord injury" (each of which is incorporated herein by reference). Buckling ratio is an estimate of relative cortical strength.

In addition, physiologic properties related to strength, such as true volumetric density of the bone or portion thereof (for example, trabecular bone, cortical bone, region of femoral neck or trochanteric region) can also be calculated by using the 3-D bone density model of the patient's femur. Additionally, thickness of the cortical shell, hip axis length, hip angle, cross sectional area of the femoral neck, and other structural parameters may also be of interest and therefore calculated.

The above-mentioned parameters have previously been calculated on 2-D DXA images (such as by Beck et al.), but can be determined more accurately by utilizing the 3-D bone density model discussed above which should improve strength (and thus fracture) prediction.

In addition to estimating bone strength, the parameters derived from the 3-D bone density model can be combined with other parameters to estimate the force of a fall.

Osteoporosis can be defined as a reduction in bone mass that increases susceptibility to fractures. A commonly used definition of osteoporosis defines a BMD less than 2.5 standard deviations (SD) below the mean for a young healthy adult woman as osteoporosis and a BMD between 1 and 2.5 SD below the mean as osteopenia. It is a common disorder, with up to 38% of women over the age of 75 classified as having osteoporosis using this definition, and is associated with high levels of morbidity, mortality, and a large cumulative cost to society.

The underlying physiologic process responsible for the development of osteoporosis is an imbalance between bone formation and resorption, and is a continuous process. During the first three decades of life, formation exceeds resorption and bone mass is increased. When peak bone mass is achieved at age 30-35, the rate of bone resorption is low and a steady state is maintained. However, beginning in the fourth or fifth decade of life, the resorption rate exceeds formation and progressive loss of bone mass occurs.

Strong risk factors for the development of osteoporosis are age and female gender. The odds of having osteoporosis are 5.9-fold higher in women aged 65-69 years, relative to women aged 50-54 years, and 14.3-fold higher in women aged 75-79 years. Low body weight and not using estrogen replacement are also associated with osteoporosis. Other risk factors for fracture or low bone density include ethnicity, history of fracture, family history of osteoporotic fracture, history of falls, low levels of physical activity, smoking, excessive alcohol or caffeine use, low calcium or vitamin D intake, and the use of various medications.

Thus, fracture prediction may be enhanced by combining strength estimates with anthropomorphic measurements such as age, height, weight, and/or bone mass index (as well as other risk factors) which contribute to the effect of the fall. Additionally, the 3-D bone density model allows study of the soft tissue overlying the hip which reduces the force on the hip. See, for example, Maitland L A, Myers E R, Hipp J A, Hayes W C, Greenspan S L, "Read my hips: measuring trochanteric soft tissue thickness," Calcif Tissue Int. (1993 February) 52(2):85-89 (incorporated in its entirety herein by reference).

Figure 4:
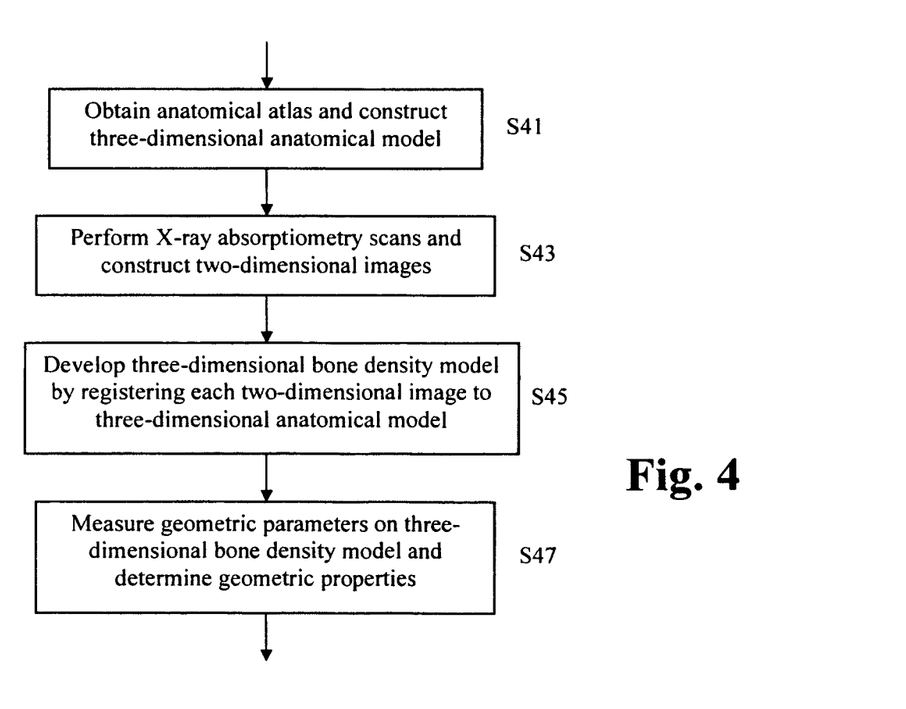
FIG. 4 shows a flow chart for another example of a method for analyzing a patient's femur to assess bone strength and/or risk of future fracture.

An example of a method for analyzing a patient's femur to assess risk of future fracture (FIG. 4) can include the following: obtain an anatomical (or statistical) atlas of a femur and construct a three-dimensional volumetric model of the femur (step S41); perform a plurality of X-ray absorptiometry scans at respective different angles of a patient's hip, collect X-ray absorptiometry data from the plurality of scans, and utilize the collected data to construct respective two-dimensional images corresponding to the plurality of scans (step S43); for each two-dimensional image, identify in the two-dimensional image a set of reference markers, map the reference markers to corresponding points of the three-dimensional anatomical model to register the two-dimensional image to the three-dimensional anatomical model, and utilize remaining points of the two-dimensional image of the patient's hip to adjust the three-dimensional anatomical model, for developing a three-dimensional bone density model of the patient's femur (step S45); and after the three-dimensional bone density model of the patient's femur is developed by registering each two-dimensional image on the three-dimensional anatomical model, perform measurements of various geometric parameters on the three-dimensional bone density model for determining geometric properties (for example, cross sectional moment of inertia, section modulus, buckling ratio, etc.), and assessing hip strength, future fracture risk and/or efficacy of therapy, such as pharmacological intervention (step S47).

The examples discussed above focused on the 3-D bone density model of a patient's femur (or hip). However, similar techniques may be applied also to the patient's spine, forearm, as well as other body parts which are susceptible to fracture. For example, X-ray absorptiometric scans may be taken of the patient's spine at several angles between 0° and 90°. In each instance, the number of scans to perform depends on the body part being scanned and also on the balancing between scan time versus information to be obtained to be obtained from the scans (as discussed above).

The improved techniques discussed herein may be implemented by software adaptation of the bone densitometer, such as the example discussed above in connection with FIGS. 2A-2C, or the QDR 4500A or Discovery A machine commercially available from Hologic, Inc., or a system including such a bone densitometer. Alternatively, the improved system can be implemented as a special-purpose machine.

The above specific embodiments and examples are illustrative, and many variations can be introduced on these embodiments and examples without departing from the spirit of the disclosure. For example, elements and/or features of different illustrative embodiments and examples may be combined with each other and/or substituted for each other within the scope of this disclosure.

What is claimed is:

1. A computer-implemented method for analyzing a patient's body part of interest to assess bone strength and/or risk of future fracture, said method comprising:
  obtaining a priori information regarding the body part of interest, said a priori information comprising a three-dimensional (3D) generic model of a comparable body part;
  performing X-ray absorptiometric scans of the patient's body part of interest and collecting X-ray absorptiometry data from the X-ray absorptiometric scans, said data being derived using x-ray imaging detectors included in a computer-driven data acquisition system, said data representing a plurality of two-dimensional (2D) images of the patient's body part, each of said 2D images of the patient's body part being at a respective orientation of an imaging x-ray beam relative to the patient's body part;
  constructing a three-dimensional model of the patient's body part of interest, by utilizing the a priori information along with the X-ray absorptiometric data, said constructing comprising operating computerized equipment to carry out the steps of:
    (i) obtaining two-dimensional (2D) projection views of the 3D generic model that correspond in orientation to the 2D images of the patient's body part,
    (ii) comparing each of the 3D projection views of the generic model with the corresponding 2D image of the patient's body part to calculate a cost function,
    (iii) modifying the 3D model according to said cost function, and
    (iv) repeating steps (i) through (iii), each time using in step (i) the 3D model as modified in the previous iteration of step (iii), until a selected threshold has been reached;
  performing measurements of various geometric parameters on the three-dimensional model as modified through said constructing, and determining at least one of geometric and structural properties of the patient's body part; and
  estimating force of a hypothetical fall by the patient;
  wherein said structural properties include bone strength, and said bone strength is considered in combination with one or more other parameters to estimate said force of the fall.

2. The method of claim 1, wherein said a priori information is obtained from an anatomical atlas or statistical atlas of the body part of interest.

3. The method of claim 1, further comprising modifying the 3D model according to said cost function in a manner that reduces a value of the cost function.

4. The method of claim 1, wherein said a priori information is obtained from an anatomical atlas or a statistical atlas of the body part of interest, said anatomical or statistical atlas utilizes eigenvectors to represent anatomical variations, and the cost function is minimized by applying a post-and-scale technique.

5. The method of claim 1, wherein said at least one of the geometric and structural properties include at least one of cross sectional moment of inertia, section modulus and buckling ratio.

6. The method of claim 1, wherein said other parameters include one or more of age, height, weight, hone mass index and soft tissue over bone.

7. A system for analyzing a patient's body part of interest to assess bone strength and/or risk of future fracture, said apparatus comprising:
  a hone densitometer configured to perform X-ray absorptiometric scans of the patient's body part of interest, collect X-ray absorptiometry data from the scans, and form a plurality of two-dimensional (2D) images of the patient's body part, each of said 2D images of the patient's body part being taken at a respective orientation of an imaging x-ray beam relative to the patient's body part; and
  a processor configured to obtain a priori information regarding the body part of interest, said a priori information comprising a three-dimensional (3D) generic model of a comparable body part, and to construct a three-dimensional model of the patient's body part of interest by:
    (i) obtaining two-dimensional (2D) projection views of the 3D generic model that correspond in orientation to the 2D images of the patient's body part,
    (ii) comparing each of the 2D projection views of the generic model with the corresponding 2D image of the patient's body part to calculate a cost function,
    (iii) modifying the 3D model according to said cost function, and
    (iv) repeating steps (i) through (iii), each time using in step (i) the 3D model as modified in the previous iteration of step (iii), until a selected threshold has been reached, and
  said processor being further configured to perform measurements of various geometric parameters on the three-dimensional model constructed by said processor and determine at least one of geometric and structural properties of the patient's body part;
  wherein said structural properties determined by said processor include bone strength, and said processor is configured to utilize said hone strength in combination with one or more other parameters to estimate force of a fall by the patient.

8. The system of claim 7, wherein said processor is configured to obtain said a priori information from an anatomical atlas or a statistical atlas of the body part of interest.

9. The system of claim 7, wherein said processor is further configured to carry out said modifying of the 3D model according to said cost function in a manner that reduces a value of the cost function.

10. The system of claim 9, wherein said processor is configured to obtain said a priori information from an anatomical atlas or a statistical atlas utilizing eigenvectors to represent anatomical variations, and the cost function is minimized by applying a post-and-scale technique.

11. The system of claim 7, wherein said at least one of the geometric and structural properties includes at least one of cross sectional moment of inertia, section modulus and buckling ratio.

12. The system of claim 7, wherein said other parameters include one or more of age, height, weight, bone mass index and soft tissue over bone.

13. A program storage device tangibly and non-transitorily embodying one or more programs of instructions executable by a computer to perform the steps of:

obtaining a priori information regarding a patient's body part of interest, said a priori information comprising a three-dimensional (3D) generic model of a comparable body part;

obtaining X-ray absorptiometry data from X-ray absorptiometric scans of the patient's body part, said data being generated using imaging x-ray detectors of a computer-driven data acquisition system, and said data representing a plurality of two-dimensional (2D) images of the patient's body part, each of said 2D images of the patient's body part being at a respective orientation of an imaging x-ray beam relative to the patient's body part;

constructing a three-dimensional model of the patient's body part of interest, by utilizing the a priori information along with the X-ray absorptiometric data;

said constructing comprising using compurter equipment for carrying out the steps of:

(i) obtaining two-dimensional (2D) projection views of the 3D generic model that correspond in orientation to the 2D images of the patient's body part, (ii) comparing each of the 2D projection views of the generic model with the corresponding 2D image of the patient's body part to calculate a cost function, (iii) modifying 3D odd according to said cost function, and (iv) repeating steps (i) through (in), each time using in step (i) the 3D model as modified in the previous iteration of step (iii), until a selected threshold has been reached; and performing measurements of various geometric parameters on the three-dimensional model as modified through said constructing and determining at least one of geometric and structural properties of the patient's body part.

* * * * *

UNITED STATES PATENT AND TRADEMARK OFFICE
CERTIFICATE OF CORRECTION

| | | |
|---|---|---|
| PATENT NO. | : 8,634,629 B2 | Page 1 of 1 |
| APPLICATION NO. | : 12/452310 | |
| DATED | : January 21, 2014 | |
| INVENTOR(S) | : Kevin E. Wilson | |

It is certified that error appears in the above-identified patent and that said Letters Patent is hereby corrected as shown below:

In the Claims

Column 14, line 7, claim 13, "3D odd" should be changed to --3D model--.

Signed and Sealed this
Twenty-seventh Day of May, 2014

Michelle K. Lee
*Deputy Director of the United States Patent and Trademark Office*